(12) United States Patent
Neumann et al.

(10) Patent No.: US 7,194,310 B2
(45) Date of Patent: Mar. 20, 2007

(54) ELECTROMEDICAL IMPLANT FOR INTERCARDIAL CORONARY THERAPY

(75) Inventors: Wiebke Neumann, Berlin (DE); Max Schaldach, Jr., Berlin (DE); Marcel Starke, Berlin (DE); Werner Uhrlandt, Berlin (DE); Juergen Drews, Pirna (DE)

(73) Assignee: Biotronik Mess- und Therapiegeraete GmbH & Co. (DE)

( * ) Notice: Subject to any disclaimer, the term of this patent is extended or adjusted under 35 U.S.C. 154(b) by 168 days.

(21) Appl. No.: 10/680,726

(22) Filed: Oct. 7, 2003

(65) Prior Publication Data
US 2004/0230250 A1    Nov. 18, 2004

(30) Foreign Application Priority Data
Oct. 9, 2002    (DE)    ................. 102 47 674

(51) Int. Cl.
*A61N 1/00* (2006.01)
(52) U.S. Cl. ...................................... 607/36
(58) Field of Classification Search ................ 607/36, 607/2, 5
See application file for complete search history.

(56) References Cited

U.S. PATENT DOCUMENTS

| 5,144,946 | A | 9/1992 | Weinberg et al. |
| 5,370,669 | A | 12/1994 | Daglow et al. |
| 5,674,260 | A | 10/1997 | Weinberg et al. |
| 5,814,090 | A | 9/1998 | Latterell et al. |
| 6,026,325 | A | 2/2000 | Weinberg et al. |
| 6,251,124 | B1 | 6/2001 | Youker et al. |
| 6,445,948 | B1 * | 9/2002 | Somdahl et al. ............... 607/2 |

FOREIGN PATENT DOCUMENTS

| DE | 100 41 728 | 3/2002 |
| WO | WO 99/06107 | 2/1999 |
| WO | WO 02/32503 | 4/2002 |

\* cited by examiner

*Primary Examiner*—George Manuel
(74) *Attorney, Agent, or Firm*—Hahn Loeser + Parks, LLP; John J. Cunniff (57) ABSTRACT

The invention concerns an electromedical implant for intracardial coronary therapy comprising an implant housing in which functional component parts of the implant, namely a circuit, a battery and the like, are disposed. It is characterized in that the battery (10) has a flat side (10.2), an underside (10.3) and a peripherally extending narrow side (10.1) and the battery (10) is arranged with its underside (10.3) on an internal base surface (18.1) of the implant housing (18) and the circuit (22) is arranged in adjacent relationship with a flat side (10.2) of the battery (10).

12 Claims, 9 Drawing Sheets

ELECTROMEDICAL IMPLANT FOR INTERCARDIAL CORONARY THERAPY

The invention relates to an electromedical implant for intracardial coronary therapy, having the features recited in the classifying portion of claim 1.

BACKGROUND OF THE ART

The electrotherapeutic treatment of cardiac arrhythmias by means of implantable cardiac pacemakers has become established as a powerful, versatile, comparatively low-risk and reliable form of treatment. Electromedical implants of that kind include numerous functional individual components which are necessary for long-lasting therapeutic treatment of the heart, which is suited to the physiological factors involved and which is as trouble-free as possible. Those components can be systematically divided into components which are disposed in a housing of the implant and components which are arranged outside the housing. The latter involve for example sensors for physiological parameters and the electrodes, by way of which a pacemaker pulse is transmitted to the atrium or ventricle myocardium. The implant housing in contrast accommodates functional components such as a battery, a circuit, telemetric means and the like.

The electromedical implant is to have a service life which is as long as possible and good compatibility. Under some circumstances those two aspects can be in conflict. Thus on the one hand the implant should be of the minimum possible structural size so that it is not perceived as troublesome by the patient after the implantation operation or indeed give rise to unwanted physiological reactions. On the other hand the battery for a long service life must be of the maximum possible capacity, which in a practical context means that the battery generally fills up markedly more than 80% of the internal space of the housing. There is therefore always the need for making the optimum possible use of the available space.

As intracardial therapy in the meantime has developed into a standard procedure which has proved its worth worldwide millions of times, it is appropriate for cost reasons to automate the process for production of the implants. The construction of current electromedical implants can in that respect be described in simplified terms as follows. All functional components such as the battery, the circuit, the telemetry unit or the like are disposed in mutually juxtaposed relationship in the implant housing. The implant housing itself is generally of a flat, elongate contour with rounded-off edges and is generally formed from two half-shell portions with a kind of snap-action mechanism comprising interengaging edges. Then, in the opened condition, the conventional arrangement with functional components mounted in mutually juxtaposed relationship on an inner base surface of the half-shell portions can be clearly seen. It will be noted that such an arrangement suffers from the disadvantage that, in assembly of the individual components, it is necessary to operate on a plurality of production axes. That makes automation more difficult and leads to increased costs. In addition the available space cannot be put to optimum use, for example because generally an expensive and complicated electrical contacting means for contacting the power-consuming components with the battery additionally has to be fitted.

U.S. Pat. No. 6,026,325 to Weinberg et al. discloses an electromedical implant having a circuit whose electronic components are arranged in stacked relationship. The individual electronic components of such a circuit are disposed perpendicularly to the heightwise extent of the implant housing on parallel substrate planes. The circuit and the further functional components such as a battery and capacitors are mounted in conventional manner in mutually juxtaposed relationship on the base surface of the implant housing.

U.S. Pat. No. 6,251,124 to Youker et al. describes a cardiac pacemaker in which a plurality of capacitors is arranged in a plurality of substrate planes in the housing. All further functional components—disposed beside the capacitors—are arranged on the inner base surface of the housing.

Furthermore, WO 99/06107 discloses a cardiac pacemaker whose circuit includes a memory unit comprising memory chips stacked in mutually superposed relationship. That is intended to minimize the structural space required for an electrical connection between the individual memory chips. As in the above-mentioned specifications, the stacked arrangement is limited to selected partial structures of the functional components of the implant.

SUMMARY OF THE INVENTION

An aspect of the present invention is to make better use of the structural space available in the housing and to optimize the construction of the implant from the point of view of a production process which can be automated and is as simple as possible.

The invention emanates from an electromedical implant for intracardial coronary therapy comprising an implant housing and functional components of the implant disposed in said housing wherein the functional components comprise a circuit and a battery and wherein the battery has a flat side, an underside and a peripherally extending narrow side and the battery is arranged with its underside on an inner base surface of the implant housing and the circuit is disposed adjacent to a flat side of the battery.

In a first advantageous configuration of the invention the circuit includes a component carrier with fitment set, on the top side of which the individual electronic components of the circuit are mounted. An underside of the component carrier and thus the circuit is arranged adjacent to the flat side of the battery. Advantageously, the circuit is fixedly mounted to the flat side of the battery, for example by means of known adhesive processes. In the depicted arrangement accordingly the flat circuits which are embodied on conventional component carriers are fixed directly on the battery, in which respect a mounting direction of battery and circuit is retained. It will be self-evident that an electrical connection to the voltage source between the battery and the circuit only needs to be of small dimensions and, in contrast to conventional electrical connections, does not have to be made by way of a joining procedure but can also be implemented in a direct plug-in configuration. Accordingly a short discrete join is possible, without discrete elements.

During discharge of the battery a slight increase in the volume of the battery occurs, as a consequence of the underlying electrochemical reaction. That discharge-induced swelling of the battery must be compensated when there is a fixed connection between the battery and the circuit as otherwise there is a threat of mechanical damage to the circuit. In a further advantageous embodiment of the invention for that purpose disposed between the flat side of the battery and the underside of the circuit are structures with which it is possible to compensate for the discharge-induced swelling of the battery. Those structures include free spaces between the battery and the circuit or joining elements which permit a relative movement of the circuit with respect to the battery.

In a further advantageous configuration of the invention the underside of the component carrier and thus the circuit is arranged adjacent to an inward side of the implant housing. The electronic components of the circuit then face in the direction of the battery. If the inward side of the half-shell portion is suitably structured the half-shell portion can function at the same time as the component carrier for the electronic components. At any event, it is possible to forego the structures for compensation of the discharge-induced swelling of the battery. In production of the implant, in a common production step, the circuit is introduced into the implant and the housing closed.

It is further advantageous if there is provided a mounting element which accommodates the circuit. The relative orientation of the fitment set or components of the circuit with respect to the battery can then be adapted to the respective requirements involved. Accordingly, the electronic components can face either in the direction of the battery or in the direction of the housing. The mounting element can be introduced into the implant without a mechanical join to the battery or only at the periphery thereof so that the mechanical stresses which occur as a consequence of the discharge-induced variation in volume cannot be diverted to the circuit.

In addition, it has proven to be advantageous if the battery does not fill all the internal base surface of the implant housing. The remaining free spaces are used in such a way that, after mounting of the constituent parts, electronic components of a great structural height project into those free spaces. The aim here is to ensure the best possible utilization of space with a small overall structural height without having to make cuts in terms of functionality.

The battery which is suitable for such single-axis construction of the electromedical implant is to be as flat as possible in terms of its contour, as the circuit and optionally further functional component parts are to be arranged adjacent to its flat side. In this connection, the use of electrochemical energy storage systems based on lithium and manganese dioxide has proven to be particularly advantageous. The equipment components of the circuit are preferably also of the minimum possible structural height.

A further preferred configuration of the invention provides that the adjacent flat sides of the battery and the circuit have a mutually matched heightwise profile. The aim here is to minimize the overall height of the two component parts which are stacked one upon the other. Thus, in regions in which electronic components of the circuit of a relatively great structural height are disposed, the battery is of a smaller structural height than in the other regions. If further or all functional component parts disposed in the implant housing are stacked one upon the other, then the above-described matching in respect of the heightwise profile can also be applied to those component parts.

A further preferred embodiment of the invention is one in which the implant housing comprises two half-shell portions and one thereof is at the same time a constituent part of the battery housing. In that way it is possible to eliminate a housing half-shell portion.

In a further development of the last-mentioned concept of the invention, both half-shell portions at the same time also form the battery housing. In this case the circuit and all further functional component parts of the implant must hermetically sealed with respect to the electrolyte of the battery. It is possible in that way to eliminate two half-shell portions and the utilization of structural space in the arrangement can be further optimized.

Further preferred embodiments of the invention are set forth by the other features recited in the appendant claims.

BRIEF DESCRIPTION OF THE DRAWINGS

The invention is described in greater detail hereinafter in embodiments with reference to drawings in which.

DETAILED DESCRIPTION OF THE INVENTION

The mode of operation and the area of use of electromedical implants are generally known. By virtue of an appropriate selection of functional components, all stimulation and diagnostic functions which are necessary for each individual case can be integrated into such an electromedical implant. It will be noted that in the present case only the arrangement according to the invention of the functional components in the implant housing is of significance. Therefore only the structural features, which are necessary to the invention, of the individual functional components and their relative position with respect to each other are described in the examples hereinafter.

FIGS. 1a through 1d are greatly simplified side and plan views showing the contours of two alternative embodiments of a battery 10. In this example the battery 10 is of an oval basic shape. While having the same base surface, that is to say the same lengthwise and widthwise dimensions, the two batteries 10 differ only in respect of their heightwise profile. The battery 10 illustrated in FIGS. 1a and 1b has a narrow side 10.1 which extends therearound at a constant height as well as a flat side 10.2 and an underside 10.3 with a flat contour, thus affording a homogenous heightwise profile. In contrast the battery 10 shown in FIGS. 1c and 1d involves a heightwise profile in which a first portion 12 of the narrow side 10.1 and the flat side 10.2 is of a smaller height than a second portion 14. The conditions under which the use of one or other alternative embodiment of the battery 10 is appropriate will be discussed in greater detail hereinafter.

Figure 1A:
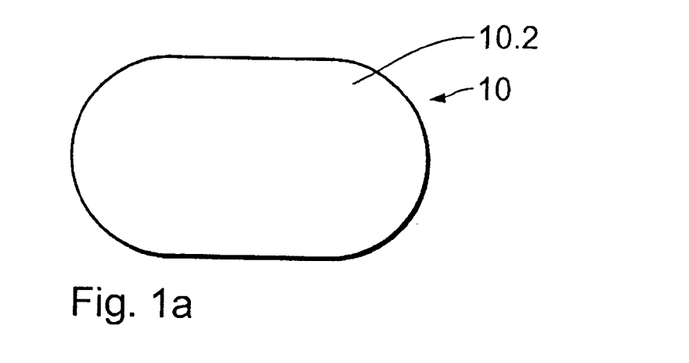
FIGS. 1a through 1d are diagrammatic plan and side views of batteries for an electromedical implant.
Figure 1B:
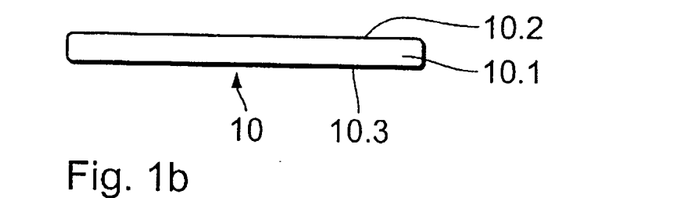
Figure 1C:
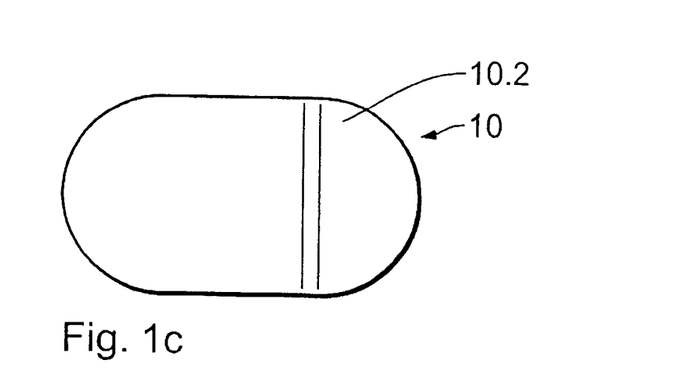
Figure 1D:
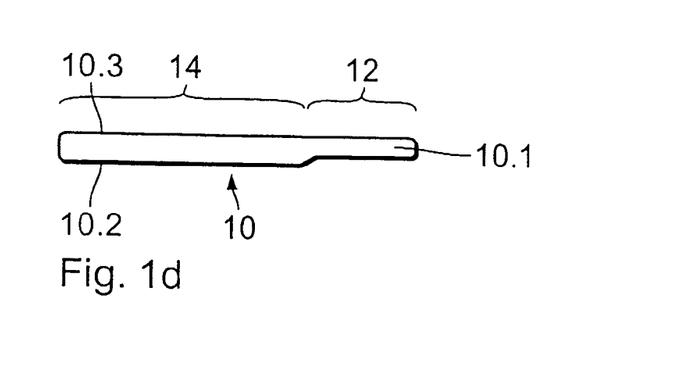
Figure 2A:
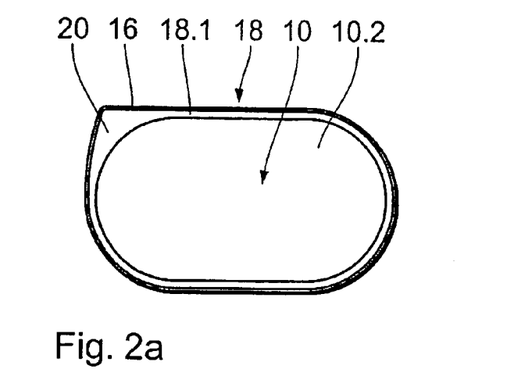
FIGS. 2a and 2b are two diagrammatic plan views onto a half-shell portion of an implant housing with a battery arranged on the internal base surface.
Figure 2B:
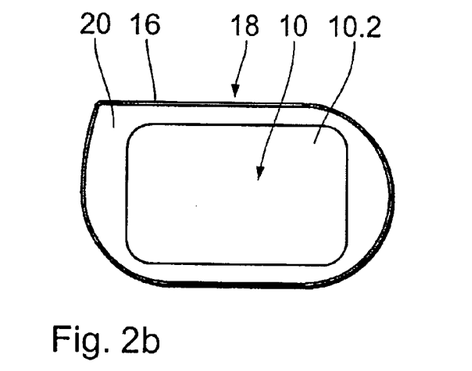

The battery itself is in particular an electrochemical cell based on lithium/manganese oxide elements. Batteries 10 of that kind are distinguished by their particularly high energy density and also their flexible design so that they are suitable as a flat unit or sandwich unit. FIGS. 2a and 2b show the relative position of two batteries 10 involving different base shapes in a half-shell portion 16 of an implant housing 18. As will be clearly apparent the battery 10 in each case does not take up an entire internal base surface 18.1 of the half-shell portion 16. Rather, free spaces 20 of differing sizes remain, and the use thereof will also be discussed in greater detail hereinafter.

Figure 3:
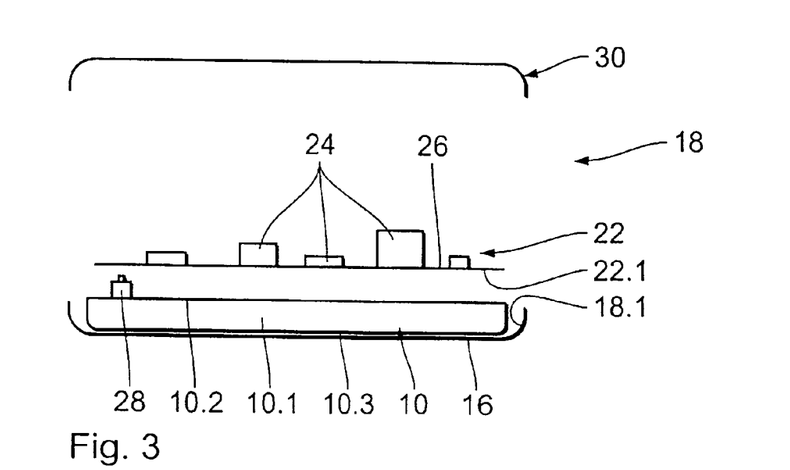
FIG. 3 is a sectional view of a circuit arrangement in the implant in accordance with a first variant.

A highly diagrammatic sectional view in FIG. 3 shows an electromedical implant including two functional component parts, namely the battery 10 and a circuit 22. The circuit 22 includes all electronic components 24 which are necessary for the functional logic of the implant and which are arranged in the form of an equipment set on a component carrier 26 with a circuit board. The electronic components 24 are preferably SMT-units which are produced in per se known manner from the point of view of a structural height which is as small as possible. An electrical connection between the battery 10 and the circuit 22 can be produced by the lead-through duct 28 indicated here. The circuit 22 is now fitted with its underside 22.1 onto the flat side 10.2 of the battery 10, in such a way that electrical contact is produced and the circuit 22 is arranged in adjacent relationship to the flat side 10.2 of the battery 10—possibly being fixed by adhesive means. Then the implant housing 18 is closed by a second half-shell portion 30 being put onto the first half-shell portion 16. The two half-shell portions 16, 30 are for that purpose preferably in the form of snap-action shell portions with mutually interengaging edges.

Figure 4:
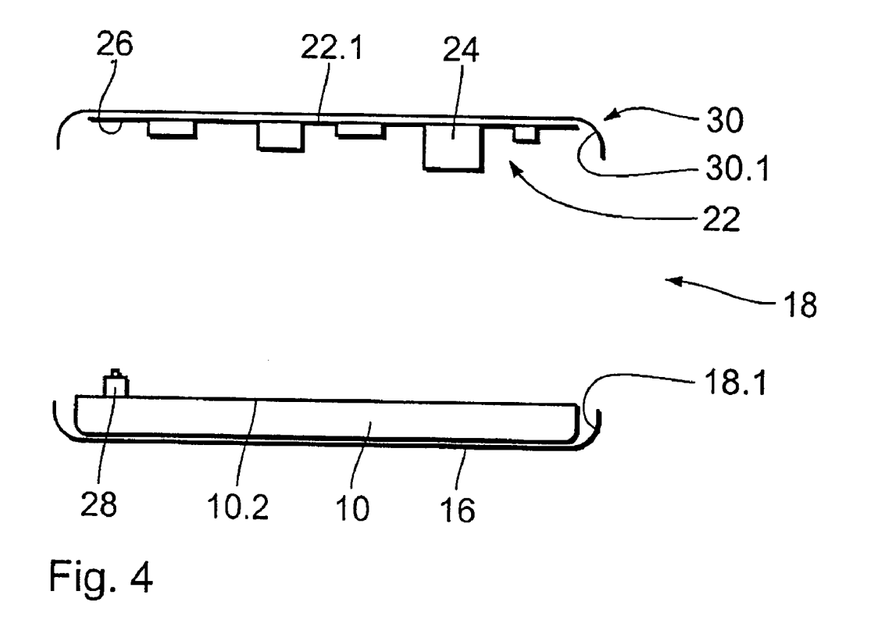
FIG. 4 is a sectional view of a circuit arrangement in the implant in accordance with a second variant.

In an arrangement which is an alternative to FIG. 3 the circuit 22 is arranged with its underside 22.1 in adjacent relationship to an inward side 30.1 of the second half-shell portion 30 (FIG. 4). The equipment set of the circuit 22 then faces in the direction of the battery 10. An electrical connection is in turn made by way of the lead-through duct 28 when the two half-shell portions 16, 30 of the implant housing 18 are brought together. The inward side 30.1 of the second half-shell portion 30 can possibly be suitably structured to carry the electronic components 24 of the circuit 22. Thus for example a component carrier can be introduced directly into the inward side 30.1 of the half-shell portion 30.

The following is to be noted in regard to the dimensioning of the individual constituent parts of the variants in FIGS. 3 and 4: an overall thickness of the battery 10 in all of the regions in opposite relationship to the circuit 22 is preferably <3.9 mm, a component height of all electronic components 24 is preferably <2 mm and the thickness of the component carrier 26 is <0.25 mm. Finally the battery 10 and the circuit 22 preferably extend over >85%, in particular over >90%, particularly preferably over >95%, of the overall housing volume. The circuit 22 preferably extends over >80% in particular over >90% and particularly preferably over >95% of the flat side of the battery 10.

Figure 5A:
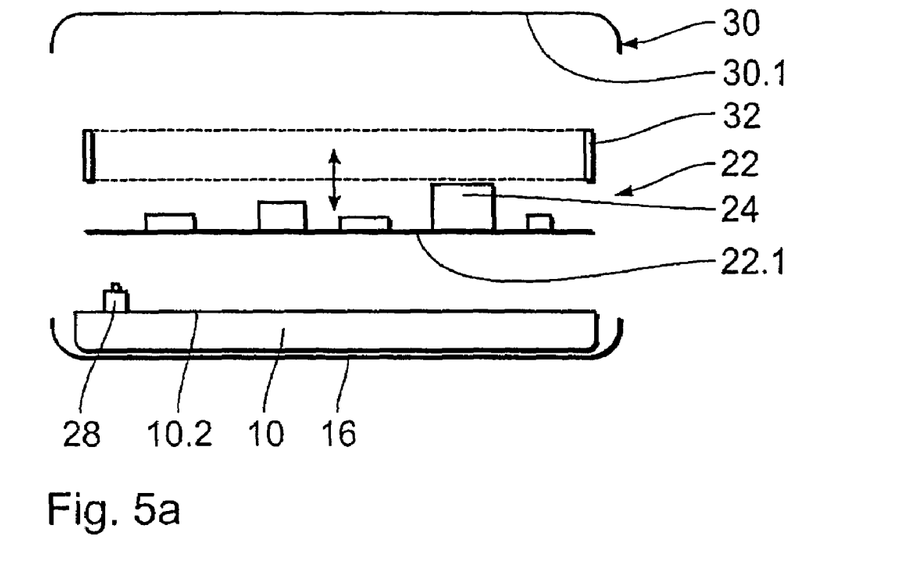
FIGS. 5a and 5b show two sectional views of alternative arrangements of the circuit with a mounting element.
Figure 5B:
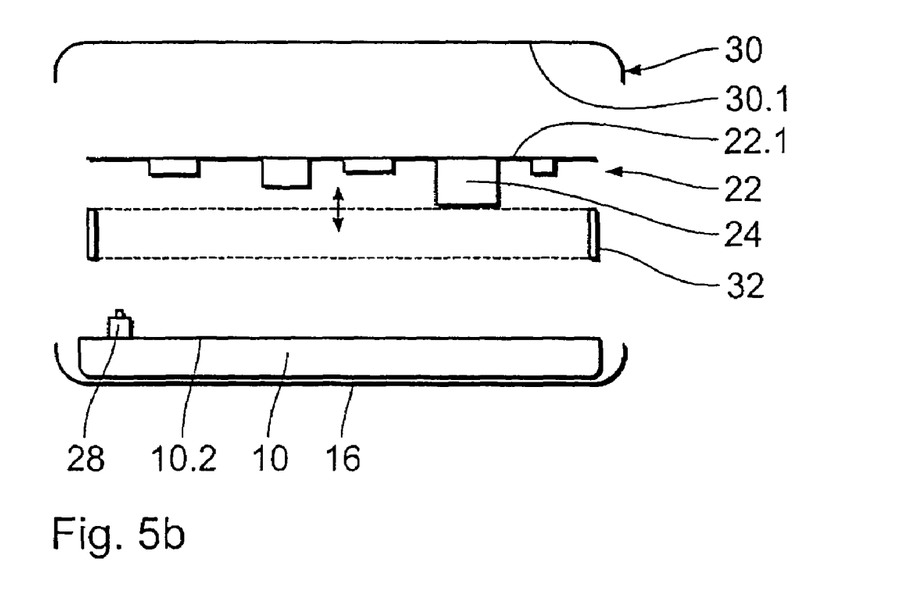

FIGS. 5a and 5b show the circuit 22 and the battery 10 in a stacked arrangement which is in principle the same, as in FIGS. 3 and 4. However, the circuit 22 does not bear directly against the battery 10 or the half-shell portion 30 but is accommodated by a mounting element 32. The mounting element 32 has structures which are suitable for that purpose and in which the component carrier 26 can be clamped. The specific design configuration of the structures must be adapted to the respective structural aspects involved. Measures of that nature are adequately known to the man skilled in the art so that they will not be discussed in greater detail here. After accommodating the circuit 22 the mounting element 32 is arranged in adjacent relationship with the battery 10, in which case the component mounting side thereof faces selectively in the direction of the half-shell portion 30 (FIG. 5a) or in the direction of the battery 10 (FIG. 5b). Such a mounting element 32 affords the advantage that stresses which can occur in the region of the battery 10 as a consequence of variations in volume are not transmitted directly to the circuit 22 and there result in mechanical damage. In addition, this arrangement affords options in terms of joining technologies which are suited to single-axis mounting operations.

Figure 6:
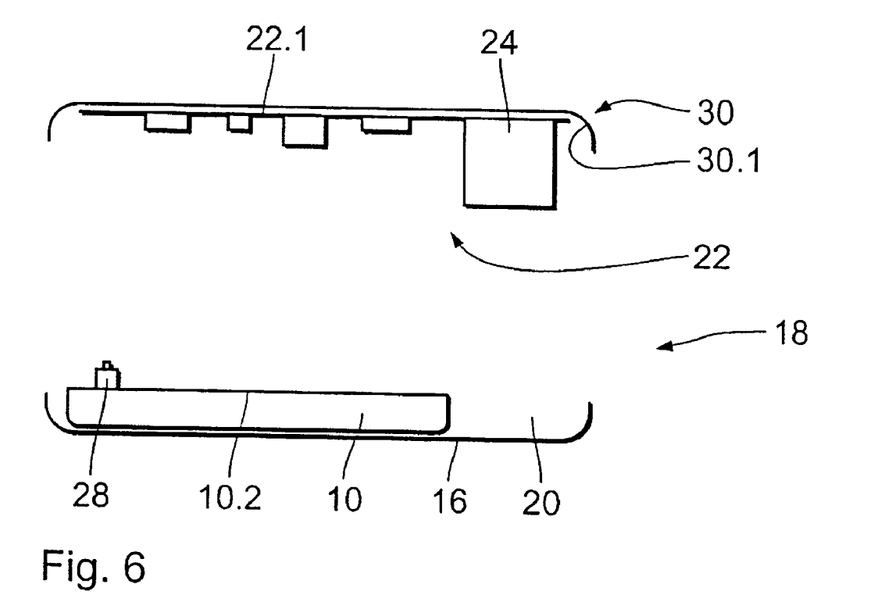
FIG. 6 shows a sectional view of a further alternative circuit arrangement in the implant with a free space in the region of the implant housing.

If the battery 10 does not occupy the entire base surface of the half-shell portion 16 of the implant housing 18 and thus free spaces 20 remain, it is possible to embody the alternative arrangement of the component parts of the implant, as is diagrammatically shown in FIG. 6. In accordance with that arrangement electronic components 24 of particularly great structural height are placed on the circuit 22 in such a way that they project into the free spaces 20, after the two component parts have been assembled.

Figure 7A:
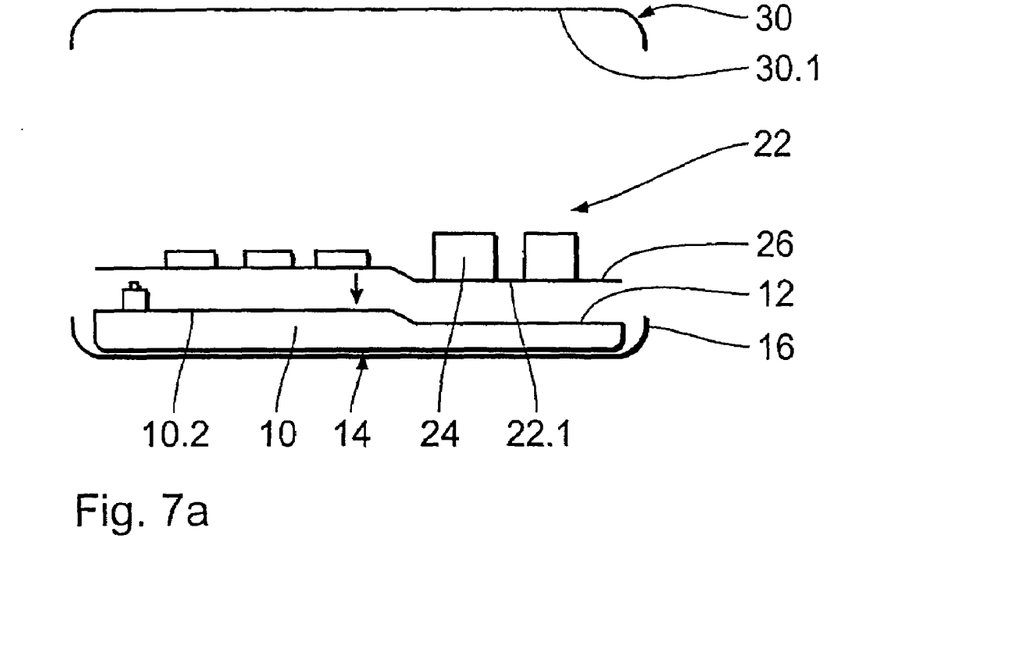
FIGS. 7a and 7b show two sectional views of alternative arrangements with a heightwise profile which is matched as between the battery and the circuit.
Figure 7B:
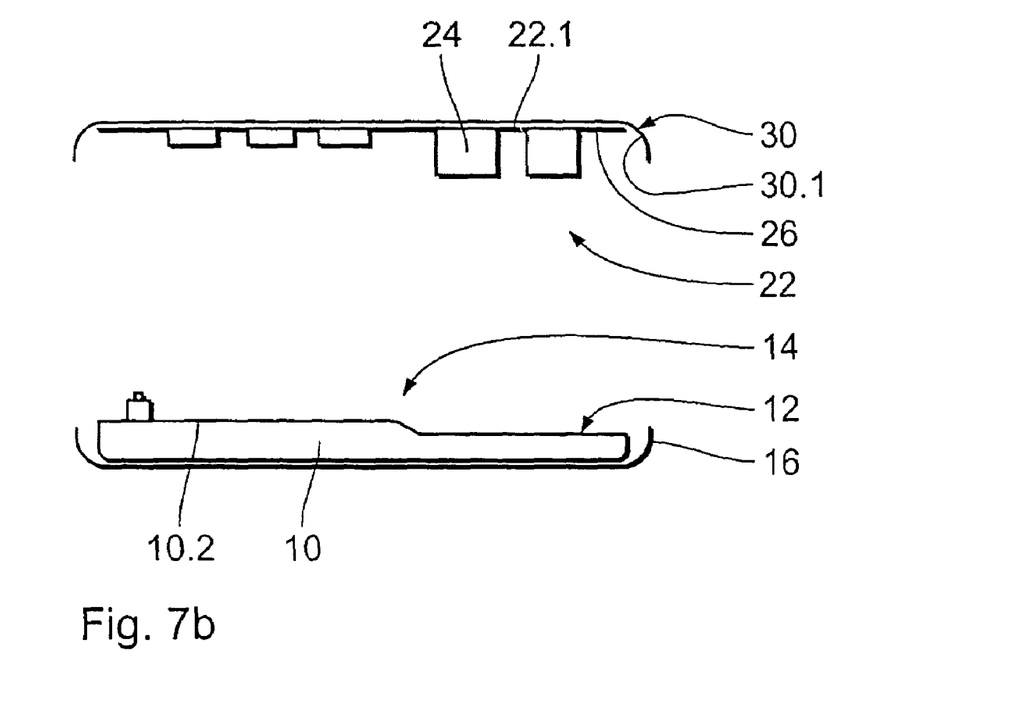
Figure 8A:
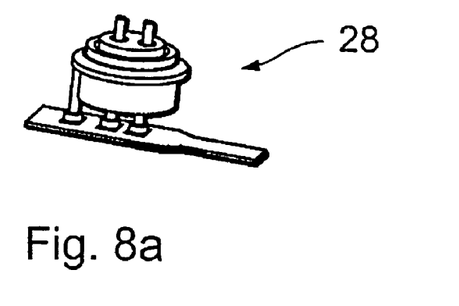
FIGS. 8a through 8f show perspective detail views of six alternative lead-through ducts for producing an electrical connection.
Figure 8B:
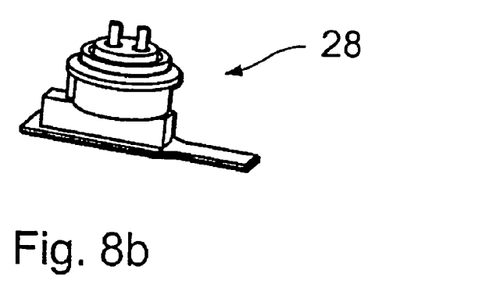
Figure 8C:
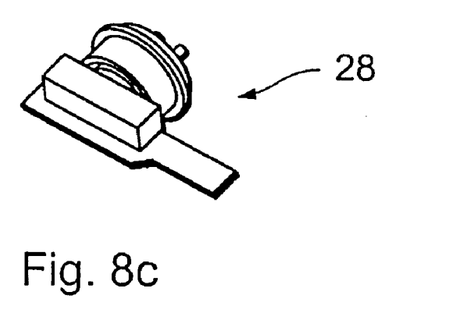
Figure 8D:
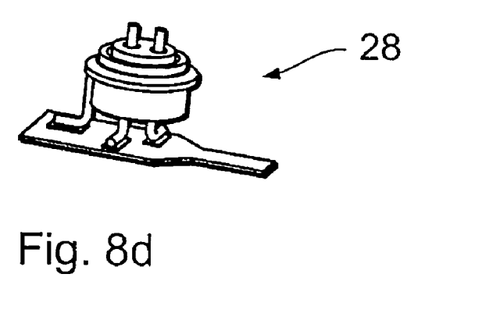
Figure 8E:
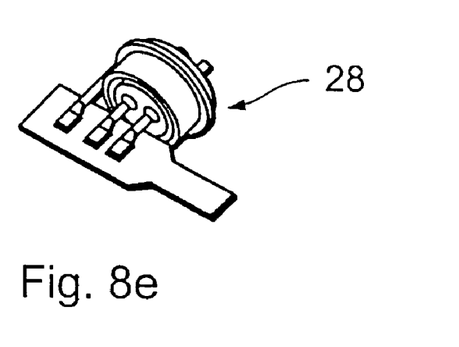
Figure 8F:
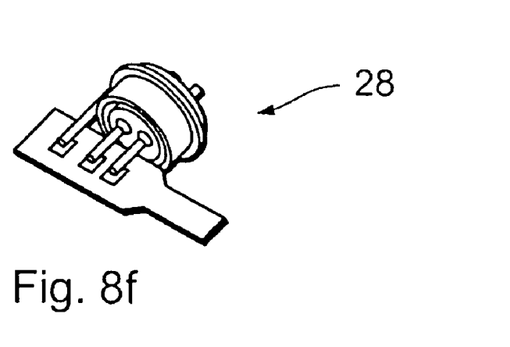

With a differing structural height in respect of the electronic components 24 of the circuit 22, two further alternative possible design options present themselves for such a single-axis arrangement of the component parts (FIGS. 7a and 7b). Both alternatives are based on a battery 10 with heightwise profile as has already been described with reference to FIG. 1b. As shown in FIG. 7a the contour of the circuit 22 including the component carrier 26 is adapted to the heightwise profile of the battery 10. The electronic components 24 of the greatest structural height are obviously disposed in the region 12 of the battery 10 which involves the smallest heightwise extent (FIG. 7a). Alternatively, as shown in FIG. 7b, a circuit 22 with a flat component carrier 26 is arranged in adjacent relationship with the half-shell portion 30, more specifically in such a way that the highest electronic components 24, after the mounting procedure, are arranged above the region 12 of the battery 10 which is of the smallest structural height.

FIGS. 8a through 8f show a total of six alternative embodiments of a lead-through duct 28 which can be used to produce the electrical connection between the battery 10 and the circuit 22. The ducts 28 can be soldered on during an SMT-mounting process as constituent parts of the circuit 22. It is necessary in each individual case to decide at what locations ultimately a soldering operation is to be effected or what orientation individual elements of the duct 28 have relative to the position of the component parts to be connected therewith. It will be noted that in principle the single-axis construction of the functional component parts permits a marked simplification in the electrical circuitry as only small distances have be bridged. That affords savings of material and gains in terms of structural space. The ducts 28 which are set forth by way of example are electrically connected to the circuit 22 by way of nail heads (FIG. 8a), adaptors (FIGS. 8b and 8c), bent pins (FIG. 8d), flattened pins (8e) or conventional solder joins (8f). In accordance with the variants in FIGS. 8b and 8c, it is possible to forego bonding joining processes for producing the electrical connection. It will be appreciated that for that purpose it is possible to provide electrical plug elements of varying configurations, which engage into each other when the implant is assembled. Here too the description will not go into these aspects in greater depth as such plug elements are sufficiently known to the man skilled in the art and have to be adapted to the respective functional and structural requirements involved, from one case to another.

Figure 9A:
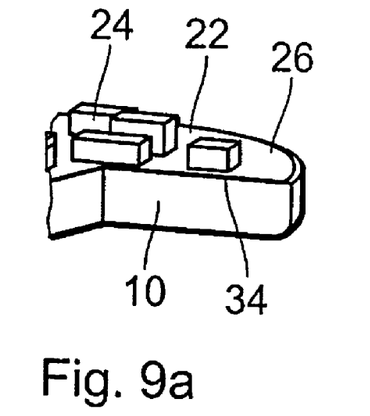
FIGS. 9a and 9b show a partly sectional view and a detail view on an enlarged scale through the battery, circuit and a structure for compensating for discharge-induced variations in volume.
Figure 9B:
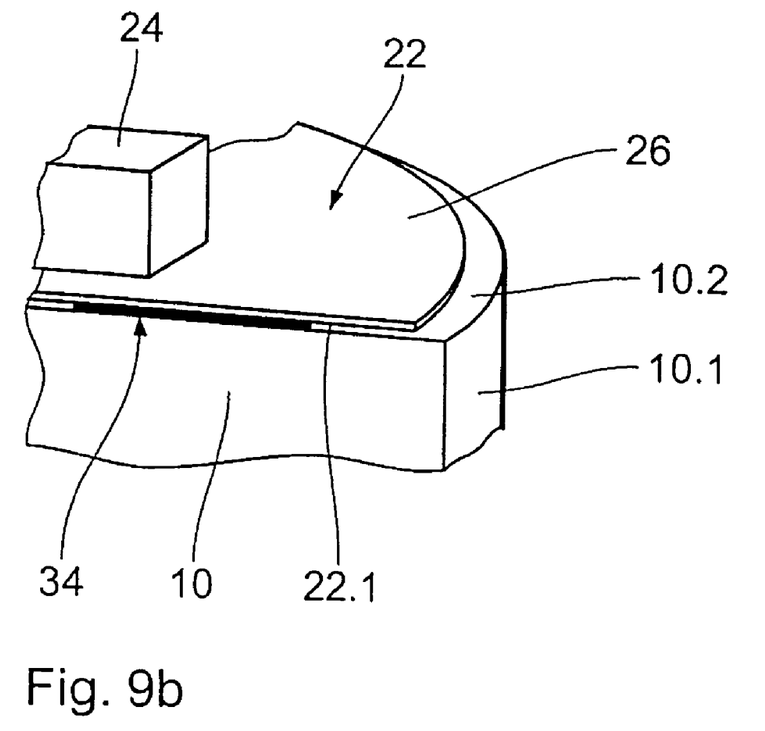

When the circuit 22 is fixedly connected to the battery 10, measures must be taken to prevent damage to the circuit 22 as a consequence of a gradual variation in volume of the battery 10. Such a variation in volume results from the electrochemical reactions which take place during the discharge process in the battery 10. To compensate for the discharge-induced swelling of the battery 10, special structures 34 are arranged between the flat side 10.2 of the battery 10 and the underside 22.1 of the circuit 22. FIGS. 9a and 9b—in part as a detail view on an enlarged scale—show a view in section through the battery 10 and the circuit 22 in the region of the structures 34. They are in the form of free spaces between the battery 10 and the circuit 22, into which parts of the battery 10 can penetrate in the discharge process and the increase in volume which is related thereto. Those structures 34 can be an integral constituent part of the component carrier 26, for example etched copper structures, and they can be inexpensively produced using standard procedures in production of the component carrier.

Figure 10A:
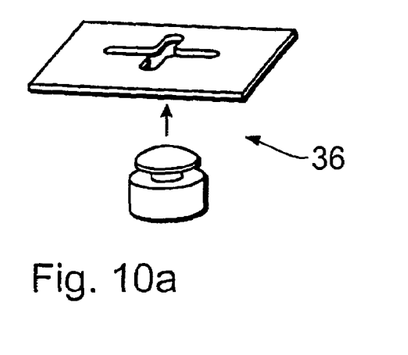
FIGS. 10a and 10b show perspective side views of two joining elements for compensating for discharge-induced variations in volume in the open and closed form.
Figure 10B:
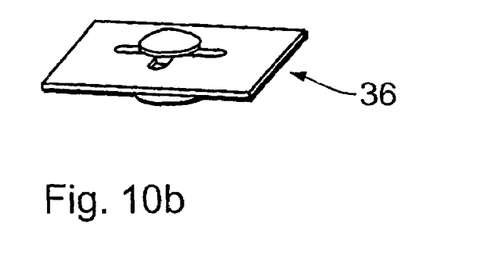

As an alternative thereto, it is also possible to provide between the battery 10 and the circuit 22 joining elements 36 as are shown in FIGS. 10a and 10b prior to and after mounting of the component parts. The joining elements 36 involve a male and a female contour which, when the component parts are stacked in mutually superposed relationship, engage one into each other and hold the component parts at a defined spacing. It will be appreciated that it is possible here to have recourse to a large number of alternative embodiments of the joining elements 36, as are sufficiently known from the state of the art. The only essential criterion in regard to the joining elements 36 is that they permit a relative movement of the two component parts with respect to each other. For automation reasons the illustration snap-action connection particularly presents itself in that respect.

Figure 11:
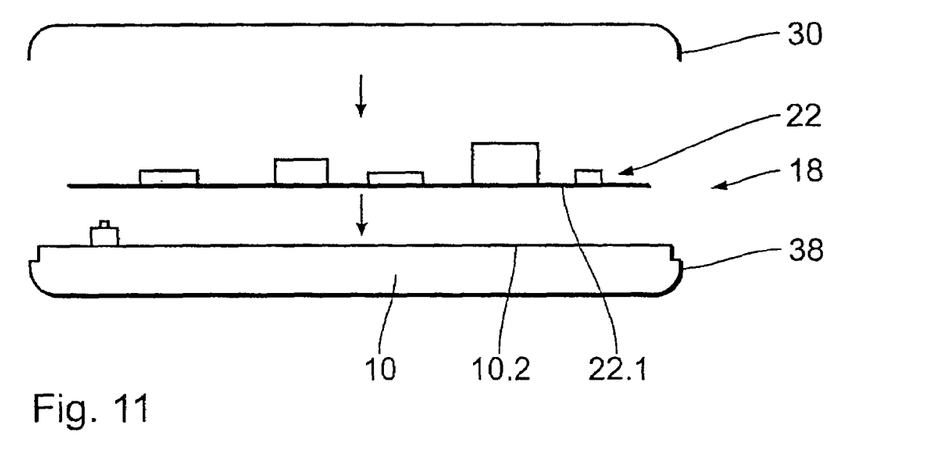
FIG. 11 is a sectional view of an arrangement in which the battery housing replaces a half-shell portion of the implant housing.

FIG. 11 diagrammatically shows a further alternative arrangement with a single-axis component construction. In its broad outlines it corresponds to the arrangement of the circuit 22 and the battery 10, which has already been described with reference to FIG. 3. It will be noted that in this case a battery housing 38 is used at the same time to form the lower half-shell portion of the implant housing 18. For that reason, at least in that region, the battery housing 38 is made from a biocompatible material, in particular titanium. In that way it is possible to forego one of the two half-shell portions of the implant housing 18 and the resulting structural space can be used for the functional component parts. In addition, a production step is eliminated from the production process, namely the step of placing the battery 10 in one of the half-shell portions of the implant housing 18. When turning over a seam between the battery housing 38 and the half-shell portion 30, if necessary (for example because of a thermal loading in the joining procedure), it is possible to implement subsequent filling of the battery 10 with electrolyte or activation in some other manner by way of an additional filling opening, whereby it is possible to determine the moment in time of the commencement of energy-consuming operation of the implant.

Figure 12:
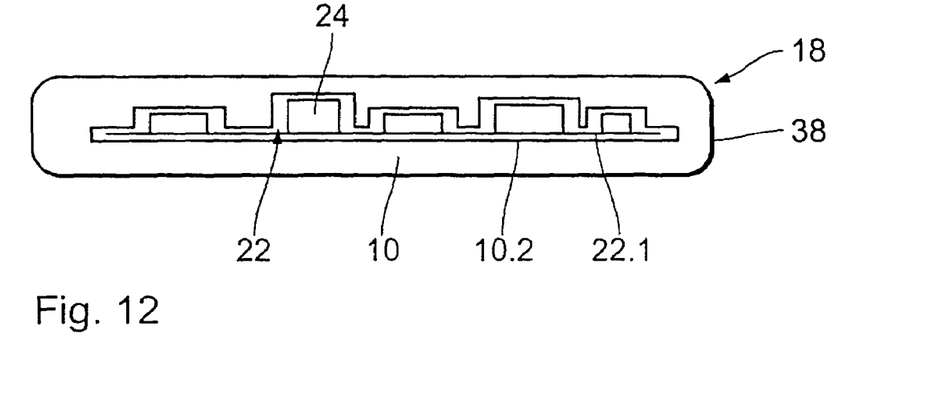
FIG. 12 shows a sectional view of an implant housing in which the battery housing replaces both half-shell portions of the implant housing.

In an extension of the last embodiment FIG. 12 is a diagrammatic sectional view of an electromedical implant in which the implant housing 18 is completely replaced by the battery housing 38. All functional component part—in this case the illustrated circuit 22 with its electronic components 24—are disposed within the battery 10 and to protect them have to be hermetically sealed in relation to the electrolyte of the battery 10. Sealing of the circuit 22 can be effected for example by a dipping process with inert resins/dipping lacquers. The dried resins/dipping lacquers form a protective layer through which the electrolyte cannot pass or which it cannot attack. It is possible in that way to eliminate two housing half-shell portions.

Figure 13:
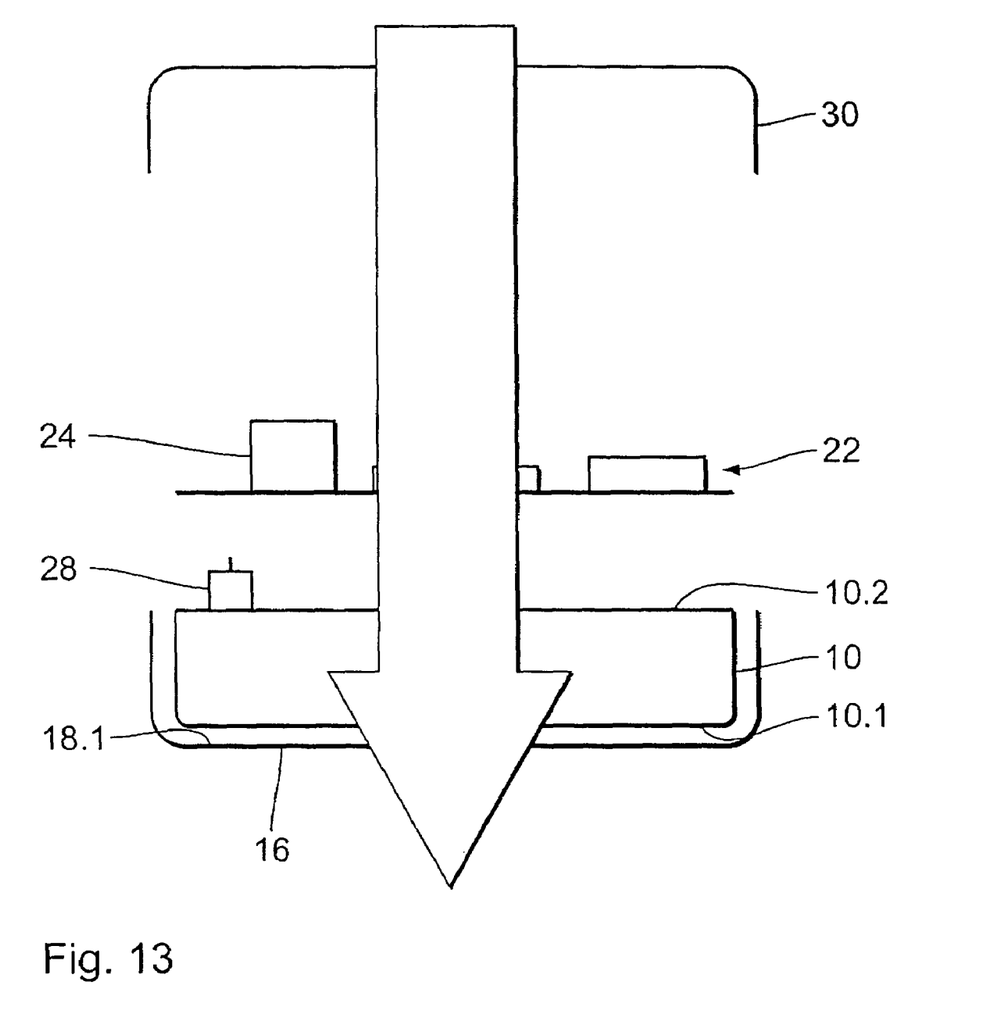
FIG. 13 shows an illustration of the single-axis production process of an electromedical implant.

FIG. 13 is intended to illustrate once again by way of example the single-axis mounting of the functional component parts during manufacture of an implant (as indicated by an arrow). Firstly the battery 10, then the circuit 22 and finally the half-shell portion 30 are respectively fitted into or onto the half-shell portion 16, in each case from the same approach direction. That substantially simplifies automation and enhances the degree of precision in terms of placement of the individual components. The arrangement and the mounting sequence may vary.

The implants produced in the above-described manner are intended to correspond in their dimensions to the dimensions of known implants. They are therefore of an overall height of between 5 and 7 mm. Of that, the metal case of the implant housing 18 including applied films for insulation and the free space for fixing of the component parts occupies between about 0.6 and 0.9 mm. In embodiments in which the battery 10 has a heightwise profile (FIGS. 7a and 7b) the thickness of the battery generally varies between 1.5 and 4.5 mm, with the remaining structural space being used for the circuit 22.

List of references

| | |
|---|---|
| 10 | battery |
| 10.1 | narrow side of the battery 10 |
| 10.2 | flat side of the battery 10 |
| 10.3 | underside of the battery 10 |
| 12 | portion of low structural height |
| 14 | portion of larger structural height |
| 16 | lower half-shell portion |
| 18 | implant housing |
| 18.1 | internal base surface |
| 20 | free space |
| 22 | circuit |
| 22.1 | underside of the circuit 22 |
| 24 | electronic components |
| 26 | component carrier |
| 28 | lead-through duct |
| 30 | upper half-shell portion |
| 30.1 | inward side of the upper half-shell portion 30 |
| 32 | mounting element |
| 34 | structures for compensation of discharge-induced swelling |
| 36 | joining element |
| 38 | battery housing |

We claim:

1. An electromedical implant for intracardial coronary therapy comprising:

an implant housing; and functional component parts of the implant disposed in said housing, wherein said functional components comprise a circuit, and a battery;

wherein said battery has a flat side, an underside and a peripherally extending narrow side and the battery is arranged with its underside on an internal base surface of the implant housing and the circuit is arranged in adjacent relationship with a flat side of the battery, and wherein the battery does not contact the internal base surface on at least one surface of the peripherally extending narrow side, creating at least one gap between the housing and the narrow side of the battery to permit relative movement of the circuit with respect to the battery;

wherein the circuit includes a component carrier which carries electronic components, and wherein an underside of the component carrier is essentially flat and adjoins the flat side of the battery;

wherein the circuit is fixed to the flat side of the battery;

further comprising structures that compensate for discharge-induced swelling of the battery.

2. The electromedical implant according to claim 1, additionally comprising a mounting element which engages the circuit.

3. The electromedical according to claim 1, wherein said component parts are disposed in the implant housing, and wherein the battery and circuit are stacked one upon the other starting from the internal base surface of the implant housing.

4. The electromedical implant according to claim 1, wherein the circuit extends over >about 80% of the flat side of the battery.

5. The electromedical implant according to claim 1, wherein the battery and the circuit occupy >about 85% of the overall volume of the housing.

6. The electromedical implant according to claim 1, wherein the circuit is attached to the battery by a lead-through duct.

7. An electromedical implant for intracardial coronary therapy comprising:
an implant housing; and
functional component parts of the implant disposed in said housing, wherein said functional components comprise a circuit, and a battery;

wherein said battery has a flat side, an underside and a peripherally extending narrow side and the battery is arranged with its underside on an internal base surface of the implant housing and the circuit is arranged in adjacent relationship with a flat side of the battery;

wherein the circuit includes a component carrier which carries electronic components, and wherein an underside of the component carrier is essentially flat and adjoins and is fixed to the flat side of the battery;

further comprising structures that compensate for discharge-induced swelling of the battery;

wherein the structures include joining elements between the battery and the circuit wherein said elements permit a relative movement of the circuit with respect to the battery.

8. The electromedical implant according to claim 7, additionally comprising a mounting element which engages the circuit.

9. The electromedical according to claim 7, wherein said component parts are disposed in the implant housing, and wherein the battery and circuit are stacked one upon the other starting from the internal base surface of the implant housing.

10. The electromedical implant according to claim 7, wherein the circuit extends over >about 80% of the flat side of the battery.

11. The electromedical implant according to claim 7, wherein the battery and the circuit occupy >about 85% of the overall volume of the housing.

12. The electromedical implant according to claim 7, wherein the circuit is attached to the battery by a lead-through duct.

* * * * *